United States Patent [19]

Graziano

[11] Patent Number: 5,314,431
[45] Date of Patent: May 24, 1994

[54] SURGICAL INSTRUMENT USED IN CONJUNCTION WITH FIXATION OF FRACTURES OR SURGICAL OSTEOTOMIES

[76] Inventor: Thomas A. Graziano, 101 Mountainview Dr., Clifton, N.J. 07013

[21] Appl. No.: 901,574

[22] Filed: Jun. 19, 1992

[51] Int. Cl.⁵ .......................... A61B 17/56
[52] U.S. Cl. .......................... 606/101; 606/53; 606/103
[58] Field of Search .............. 606/101, 103, 104, 83, 606/86, 53, 205; 72/409, 410, 387, 388; 140/105, 106

[56] References Cited

U.S. PATENT DOCUMENTS

| | | | |
|---|---|---|---|
| 1,409,835 | 3/1922 | Doble | 72/409 X |
| 2,625,067 | 1/1953 | Stone et al. | 72/409 |
| 2,948,171 | 8/1960 | Lucibello | 72/409 |
| 3,357,460 | 12/1967 | Gawura | 140/106 |
| 3,364,724 | 1/1968 | Schmidt | 72/409 |
| 3,423,984 | 1/1969 | Keymer | 72/409 X |
| 3,429,173 | 2/1969 | Waddell | 72/409 |
| 3,804,132 | 4/1974 | Mann | 140/106 |
| 3,847,037 | 11/1974 | Fox | 72/409 X |
| 4,028,756 | 6/1977 | Couto | 140/106 X |
| 4,073,179 | 2/1978 | Hickey et al. | 72/409 |
| 4,462,403 | 7/1984 | Martin | 606/83 |
| 4,651,554 | 3/1987 | Grudzinskas | 72/410 |
| 4,733,663 | 3/1988 | Farley | 606/83 |
| 4,990,148 | 2/1991 | Worrick, III et al. | 606/83 |
| 5,084,935 | 2/1992 | Kalthoff | 72/409 X |

OTHER PUBLICATIONS

Zimmer News Release, Product News, New Neuro Instruments, Nov. 1, 1966.
Zimmer News Release, Product News, Colclough Laminectomy Rongeurs, Oct. 1966.

*Primary Examiner*—Robert A. Hafer
*Assistant Examiner*—Brian E. Hanlon
*Attorney, Agent, or Firm*—Anthony F. Cuoco

[57] ABSTRACT

A pair of pivotally attached handles are normally displaced away from each other via a spring biasing arrangement, and are displaced toward each other as by squeezing the handles against the spring bias. A wire or pin is introduced into a fixed fracture or osteotomy and an end thereof is received in an angled slot at an operating portion of one of the handles so that when the handles are squeezed against the spring bias the operating portions of both of the handles cooperate to bend the wire or pin to prevent migration or skin puncture, as the case may be.

3 Claims, 2 Drawing Sheets

SURGICAL INSTRUMENT USED IN CONJUNCTION WITH FIXATION OF FRACTURES OR SURGICAL OSTEOTOMIES

BACKGROUND OF THE INVENTION

This invention relates generally to surgical instruments and, particularly, to a surgical instrument for stabilizing and bending a wire or pin such as used after either internal or external fixation of fractures or surgical osteotomies.

When a fracture or osteotomy of a bone is surgically fixed, it is necessary to hold the fracture or osteotomy in place until healing occurs. This is often accomplished via a wire or pin, or the like which is left buried under the patient's skin or exposed external the skin. After the pin or wire is introduced it is usually bent to prevent migration or skin puncture, as the case may be.

Prior to the present invention, the aforenoted bending has been accomplished using a pair of clamps. One of the pair of clamps is used to stabilize the position of the wire or pin and the other clamp is used to bend same. With an arrangement of the type described, there is the danger of losing the desired stability while manipulating the wire or pin.

The applicant is aware of the following patents which relate generally to wire manipulating apparatus.

U.S. Pat. No. 3,421,553 which issued to Redman on Jan. 14, 1966 (U.S. Class 140-106), discloses wire-bending pliers, which are provided with integral cutoff blade portions (20) and (22), column 2, lines 9-10, as shown in FIGS. 1 and 3. These blades are immediately adjacent the portion of the pliers adapted to receive a piece of wire. If a piece of wire is engaged between faces (28) and (30), and the pliers are squeezed, then two 90 degree bends are imparted to the wire to form a substantially Z-shaped right angled stepped or joggled portion (40), column 2, lines 42-45, as shown in FIGS. 4 and 5.

U.S. Pat. No. 3,357,460 which issued to Gowura on Oct. 12, 1965 (U.S. Class 140-106), discloses a wire-forming implement, which can be operated in the same manner as a pair of pliers. As shown in FIGS. 4 and 5, a wire (54) may be inserted into the implement, and after the handles are squeezed, the implement imparts two 90 degree bends in the wire, as shown in FIG. 7 (column 2, lines 48-55).

U.S. Pat. No. 2,591,649 which issued to Whiting on Jan. 13, 1948 (U.S. Class 7-5.4) discloses a wire former and stripper, which is also operated in the same manner as a pair of pliers. A portion of the wire which has been stripped of insulation may be placed into the device, and when the device is compressed, it imparts a generally U-shaped bend in the wire, as shown by FIG. 7.

U.S. Pat. No. 715,674 which issued to Lemon on Dec. 9, 1902 (no class indicated) discloses a pin bender, which is likewise operated in the same manner as a pair of pliers. When a pin is placed into the device, and the device is compressed, two 90 degree bends are imparted to the pin, as shown by FIG. 4.

None of the above patents teaches or suggests the structure of the present invention as will be hereinafter described. Moreover, these patents relate to devices such as used by electricians, mechanics, or the like and are not within the confines of the surgical instrument art as is the present invention.

SUMMARY OF THE INVENTION

This invention contemplates a surgical instrument used in conjunction with fixation of fractures or surgical osteotomies, including a pair of handles pivotally attached to each other and normally displaced away from each other via a spring biasing arrangement. The handles are displaced toward each other by squeezing the handles against the spring biasing arrangement. A wire or pin is introduced into a fixed fracture or osteotomy and an end thereof is received in an angled slot at an operating end of one of the handles. When the handles are squeezed against the spring biasing arrangement the operating ends of both of the handles cooperate for bending the wire or pin to prevent migration or skin puncture as is desireable. An angled cannulation at the end of each handle opposite the operating end thereof is arranged for flush bending of the wire or pin as may be desireable. With the arrangement described, the pin or wire is simultaneously stabilized and bent, therefore securing the fixation of a fracture or surgical osteotomy, as the case may be.

DETAILED DESCRIPTION OF THE INVENTION

Figure 1:
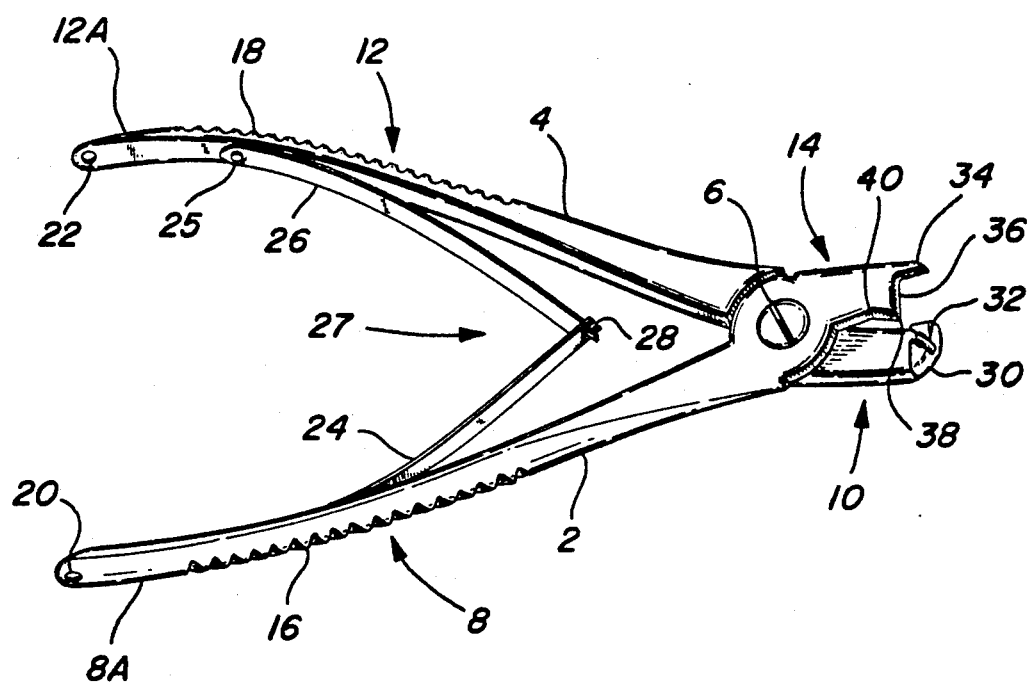
FIG. 1 is an isometric representation illustrating a surgical instrument in accordance with the invention.

With reference to the drawings and with particular reference first to FIG. 1, the instrument of the invention includes a pair of handles designated by the numerals 2 and 4. Handles 2 and 4 are pivotally attached, each to the other, via a pivot member 6.

With the instrument oriented as shown, handle 2 has a rearwardly extending grasping portion 8 and a forwardly extending operating portion 14, and handle 4 has a rearwardly extending grasping portion 12 and a forwardly extending operating portion 10. Each of the grasping portions 8 and 12 has a gripping section 16 and 18, respectively. The endmost part 8A of grasping portion 8 carries an angled cannulation 20, and the endmost part 12A of grasping portion 12 carries an angled cannulation 22. The purpose of angled cannulations 20 and 22 will be hereinafter described.

An arcuate spring-like member 24 is mounted at one end to handle 2 as by a mounting member 25 and an arcuate spring-like member 26 is likewise mounted at one end to handle 4. One of the spring-like members such as 24 carries a slot 28 at its free end thereof and which slot 28 receives the free end of the other spring-like member 26. Thus, spring-like members 24 and 26 are arranged with handles 2 and 4, respectively, in wishbone-like fashion to provide a spring biasing arrangement 27, whereby handles 2 and 4 and operating portions 14 and 10 thereof, respectively, are normally spring biased away from each other as shown in the Figure.

Operating portion 10 of handle 4 terminates in a rearwardly and upwardly extending step 30. Step 30 has an angularly and transversely extending slot 32.

Operating portion 14 terminates in an angularly and forwardly extending lip 34. An edge 36 extends away from lip 34 toward step 30 and terminates at a corner 38. An edge 40 extends rearwardly away from corner 38, first angularly away from operating portion 10 and then angularly toward said operating portion.

The purpose of step 30, slot 32, lip 34, edge 36, corner 38 and edge 40 will become evident from the further description of the invention which follows.

Figure 2:
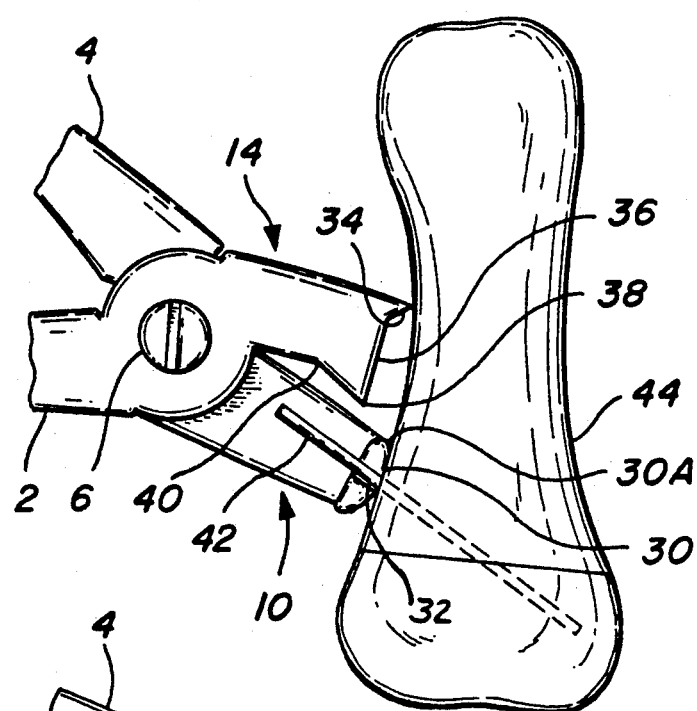
FIG. 2 is a diagrammatic representation particularly illustrating the operating portions of the instrument and showing a pin or wire inserted in a bone member and received in one of said operating portions.

With particular reference now to FIG. 2, a pin or wire 42 is temporarily inserted to hold a fracture or osteotomy of a bone member 44 in place until healing occurs after which the pin or wire is removed, or the pin or wire, which extends beyond the bone member, may be permanently inserted, as the case may be. The pin or wire may be left buried under a patient's skin or exposed external thereto. After the pin or wire is inserted into the bone member, it is usually bent to prevent migration or skin puncture, as may occur. It will be understood that pin or wire 42 is preferably a Kirschner wire of the type well known in the art and will be hereinafter referred to as "K-wire" when further describing the invention.

Thus, after K-wire 42 is inserted into bone member 44 as by conventional means and methods well known in the art, bending of the K-wire is accomplished. During the bending process, it is important that the K-wire is stabilized. That is to say, the wire must remain in the inserted position so as not to move from one position to another during bending. The present invention accomplishes this result as will be discerned.

Figure 3:
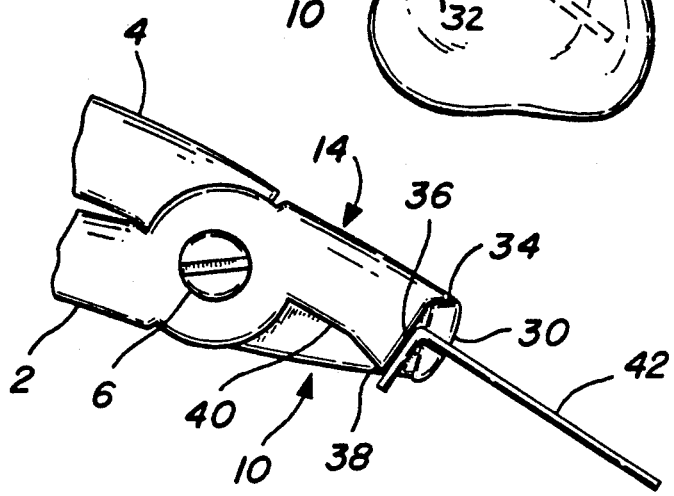
FIG. 3 is a diagrammatic representation particularly illustrating the operating portions of the instrument in cooperative engagement and showing a pin or wire as bent thereby.

As best illustrated in FIG. 2, after insertion, K-wire 42, previously cut to a desired length, is received in slot 32 so that an end thereof extends from the slot. As best illustrated in FIG. 3, handles 2 and 4 are squeezed as by a surgeon against the spring bias of arrangement 27, whereupon edge 36, corner 38 and edge 40 engage K-wire 42 and cooperatively operate to bend the K-wire as will be discerned from FIGS. 2 and 3. In this regard, it will be noted that lip 34 acts as a stop for limiting the bend to a desired angle when the lip abuts the end 30A of step 30. In this regard, it will be understood that a typical arrangement is such that for a K-wire of approximately 0.062 inches in diameter, the wire will be bent approximately ninety degrees. For smaller wire diameters, the bend will be slightly less than ninety degrees, as will be readily understood.

K-wires commonly used are 0.045 inches in diameter and 0.062 inches in diameter, and are of a suitable hardened stainless steel. The instrument of the invention is of specially hardened, wear resistant stainless tool steel. This is necessary in consideration of the wear characteristics on the several sections of operating portions 10 and 14, and particularly in consideration of the wear characteristics on corner 38 which bears the full impact of the required bending force exerted by squeezing handles 2 and 4 against the earlier described spring biasing arrangement.

Figure 4:
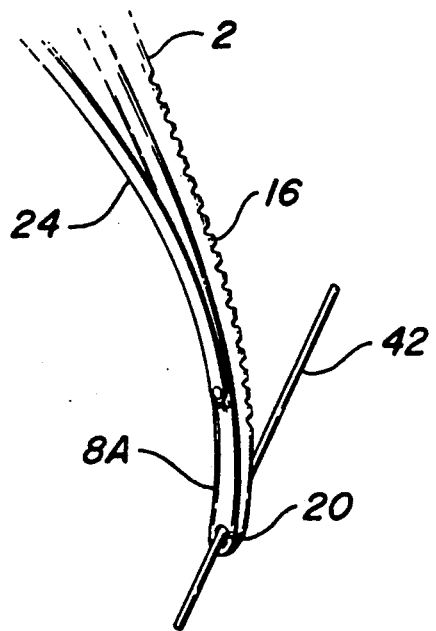
FIG. 4 is an isometric representation illustrating an alternate form of the invention for bending the pin or wire.

An alternate form of the invention for bending K-wire 42 is illustrated in FIG. 4 wherein angled cannulations 20 and 22 are utilized. This form of the invention is illustrated and described, for purposes of example, with relation to angular cannulation 20 with the same description applying to angular cannulation 22, as will be readily understood.

Thus, a K-wire such as 42 is inserted into a bone member such as 44 (FIG. 2). The K-wire is threaded through angled cannulation 20 or 22, as the case may be, and thereafter handle 2 or 4, as the case may be, is manipulated to bend K-wire 42 to an appropriate angle. This feature of the invention is useful under certain circumstances where sufficient manipulating space is available for the surgeon to bend the K-wire via cannulations 20 and 22, as the case may arise.

There has thus been described a surgical instrument which is used in conjunction with fixation of fractures or surgical osteotomies which stabilizes and bends a wire simultaneously and with one-handed operation. The instrument is easy to use and requires minimal force exerted on the part of the surgeon to achieve the desired bending.

The particular instrument described is useful for either internal or external wire fixation of fractures or osteotomies as well as after stabilization of digits or small joint dislocations. The instrument is thus advantageously used by orthopedic surgeons, podiatric surgeons, veterinarians, and the like.

With the above description of the invention in mind, reference is made to the claims appended hereto for a definition of the scope of the invention.

What is claimed is:

1. A surgical instrument used in conjunction with fixation of fractures or surgical osteotomies, comprising:

first and second handle members;

means for pivotally mounting the first and second handle members, each to the other;

the first handle member having a grasping end and an operating end;

the second handle member having a grasping end and an operating end;

means for biasing the first and second handle members so that the grasping and operating ends thereof are normally spaced apart;

the operating end of one of the first and second handle members arranged for receiving a wire which is capable of being inserted into a fixed bone member so as to extend therefrom said wire extending from said one operating end of one of the first and second handle member;

said operating end of one of the first and second handle members including an upwardly extending step having a front end and a back end, and extending in length from said front end to said back end toward the grasping end of the one handle member;

the step including a slot extending angularly across said step from said front end to said back end;

the wire extending from the one operating end having an end which is received in the slot;

the operating end of the other of the first and second handle members including a lip which extends away from the grasping end of the other handle member, a first edge which extends substantially normal to and away from the lip toward the operating end of the one handle member, said edge terminating in a corner, and a second edge having first and second linear portions which extend away from the corner, said first linear portion extending angularly toward the grasping end of the one handle member and said second linear portion extending angularly toward the grasping end of the other handle member;

the lip, the first and second edges, and the corner being in cooperative arrangement with the step, with the corner engaging the wire extending from the one operating end when the grasping ends of the first and second handle members are squeezed, whereupon the operating ends of the first and second handle members are displaced toward each other, to bend said wire;

the grasping end of each of the first and second handle members including an angle cannulation; and said wire being receivable in one of said angled cannulations for being bent.

2. A surgical instrument as described by claim 1, including:

the lip abutting the step when the operating ends of the first and second handle members are displaced toward each other to limit the extent to which the wire is bent.

3. A surgical instrument as described by claim 1, wherein the means for biasing the first and second handle members includes:

a first arcuate spring member mounted at one end to the first handle member and having a free end;

a second arcuate spring member mounted at one end to the second handle member and having a free end;

the free end of one of the first and second spring members having a groove for receiving the free end of the other of the first and second spring members; and the first and second spring members being thereupon arranged with the first and second handle members, respectively, in wishbone-like fashion to provide the spring biasing means.

* * * * *